United States Patent
Mirho

(10) Patent No.: US 9,898,453 B1
(45) Date of Patent: Feb. 20, 2018

(54) MACHINE CONTROLS FOR RAPID NUMBERING OF GRAPHICAL DEPICTIONS ON A DISPLAY SURFACE

(71) Applicant: TurboPatent Inc., Seattle, WA (US)

(72) Inventor: Charles A Mirho, Lake Oswego, OR (US)

(73) Assignee: TurboPatent Corp., Seattle, WA (US)

( * ) Notice: Subject to any disclaimer, the term of this patent is extended or adjusted under 35 U.S.C. 154(b) by 0 days.

(21) Appl. No.: 15/374,986

(22) Filed: Dec. 9, 2016

Related U.S. Application Data

(60) Provisional application No. 62/265,184, filed on Dec. 9, 2015.

(51) Int. Cl.
| | |
|---|---|
| *H04N 1/00* | (2006.01) |
| *G06F 17/24* | (2006.01) |
| *G06T 11/60* | (2006.01) |
| *G06F 3/0484* | (2013.01) |
| *G06F 3/147* | (2006.01) |
| *G06F 3/0481* | (2013.01) |
| *G06F 3/14* | (2006.01) |
| *G06F 1/00* | (2006.01) |
| *G06F 19/00* | (2018.01) |

(52) U.S. Cl.
CPC .............. *G06F 17/241* (2013.01); *G06F 1/00* (2013.01); *G06F 3/0484* (2013.01); *G06F 3/04812* (2013.01); *G06F 3/147* (2013.01); *G06F 3/1431* (2013.01); *G06F 19/708* (2013.01); *G06T 11/60* (2013.01); *G06F 3/04842* (2013.01); *G06F 3/04845* (2013.01); *G06T 2200/24* (2013.01)

(58) Field of Classification Search
CPC ........ G06F 17/241; G06F 3/0484; G06F 1/00; G06F 3/1431; G06F 3/147; G06F 19/708; G06F 3/04812; G06F 3/0482; G06F 3/04842; G06F 3/04845; G06T 11/60; H04N 1/00; H04N 1/00557
USPC ......................................................... 715/232
See application file for complete search history.

(56) References Cited

U.S. PATENT DOCUMENTS

| | | | | |
|---|---|---|---|---|
| 3,786,482 | A * | 1/1974 | Puckett, Jr. .............. | G09G 1/10 315/365 |
| 4,181,954 | A * | 1/1980 | Rosenthal ............. | G06F 17/509 358/1.3 |
| 5,338,034 | A * | 8/1994 | Asch ...................... | A63F 9/088 273/153 P |
| 6,233,351 | B1 * | 5/2001 | Feeney .............. | G06K 9/00416 345/522 |
| 2009/0055413 | A1 * | 2/2009 | Audet ............... | G06F 17/30994 |

* cited by examiner

*Primary Examiner* — Cesar Paula
*Assistant Examiner* — Luu-Phuong Nguyen
(74) *Attorney, Agent, or Firm* — FSP LLC

(57) ABSTRACT

A process for rapid numbering of a drawings panel on a graphical user interface gathers geometric location information relative to a drawings panel from actions performed on a machine interface. The process generates an element number using a sequencer that has been configured with a numbering schema. The number is then associated with the geometric location of the action performed on the machine interface, and checks for any unnumbered graphical elements at the same location which it also associates with the number. The element number is stored to a number set and populated on the drawings panel at the geometric location of the performed action.

5 Claims, 16 Drawing Sheets

MACHINE CONTROLS FOR RAPID NUMBERING OF GRAPHICAL DEPICTIONS ON A DISPLAY SURFACE

CROSS-REFERENCE TO RELATED APPLICATIONS

This application claims priority and benefit under 35 U.S.C. 119 to U.S. application Ser. No. 62/265,184, filed on Dec. 9, 2015, titled "MACHINE CONTROLS FOR RAPID NUMBERING OF GRAPHICAL DEPICTIONS ON A DISPLAY SURFACE" and which is incorporated herein by reference in its entirety.

BACKGROUND

Conventional drawing programs provide for numbering of graphical elements in a drawing via text boxes that are configured with numbers and placed proximate with the element to number. Stem lines may be added between the number and the element. Numbering this manner may be slow and time consuming, reducing productivity.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

Figure 1:
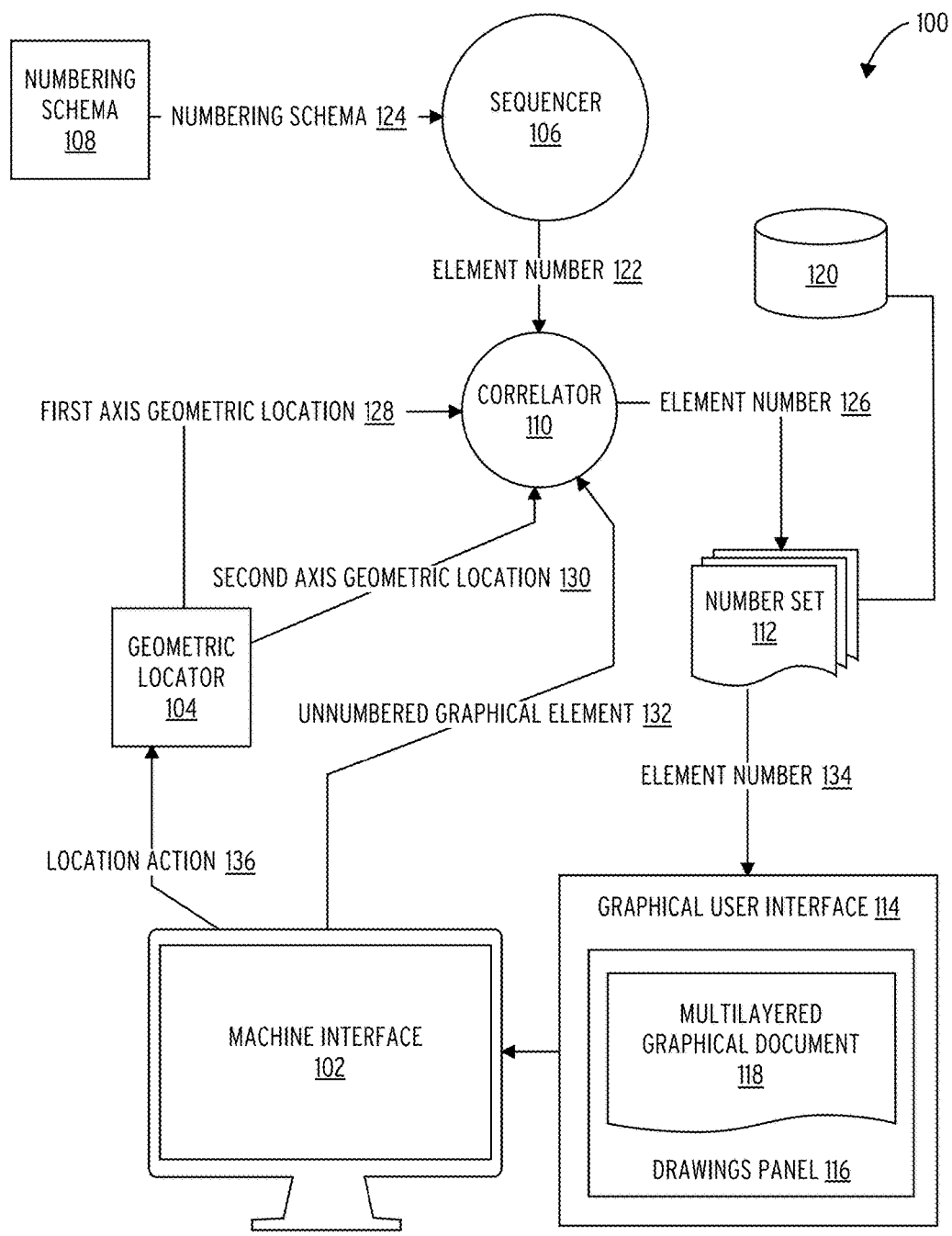
FIG. 1 illustrates a rapid sequencer for a graphical user interface 100 in accordance with one embodiment.

References to "one embodiment" or "an embodiment" do not necessarily refer to the same embodiment, although they may. Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively, unless expressly limited to a single one or multiple ones. Additionally, the words "herein," "above," "below" and words of similar import, when used in this application, refer to this application as a whole and not to any particular portions of this application. When the claims use the word "or" in reference to a list of two or more items, that word covers all of the following interpretations of the word: any of the items in the list, all of the items in the list and any combination of the items in the list, unless expressly limited to one or the other. Any terms not expressly defined herein have their conventional meaning as commonly understood by those having skill in the relevant art(s).

Terms used herein have their conventional meaning in the relevant arts unless otherwise defined below:

"Associator" in this context refers to a correlator (see the definition for Correlator).

"Circuitry" in this context refers to electrical circuitry having at least one discrete electrical circuit, electrical circuitry having at least one integrated circuit, electrical circuitry having at least one application specific integrated circuit, circuitry forming a general purpose computing device configured by a computer program (e.g., a general purpose computer configured by a computer program which at least partially carries out processes or devices described herein, or a microprocessor configured by a computer program which at least partially carries out processes or devices described herein), circuitry forming a memory device (e.g., forms of random access memory), or circuitry forming a communications device (e.g., a modem, communications switch, or optical-electrical equipment).

"Classifier" in this context refers to a specific type of correlator/associator logic that associates one or more inputs with a category, class, or other group sharing one or more common characteristics. An example of a classifier that may commonly be implemented in programmable hardware is a packet classifier used in network switches, firewalls, and routers (e.g., packet classifiers utilizing Ternary Content Addressable Memories). An example software or firmware classifier is: if (input1.value<12.5) input1.group=group1; else if (input1.value>=12.5 and input1.value<98.1) input1.group=group2; else input1.group=group3; Other examples of classifiers will be readily apparent to those of skill in the art, without undo experimentation.

"Combiner" in this context refers to a logic element that combines two or more inputs into fewer (often a single) output. Example hardware combiners are arithmetic units (adders, multipliers, etc.), time-division multiplexers, and analog or digital modulators (these may also be implemented is software or firmware). Another type of combiner builds an association table or structure (e.g., a data structure instance having members set to the input values) in memory for its inputs. For example: val1, val2, val3→combiner logic→{val1, val2, val3} set.val1=val1; set.val2=val2; set.val3=val3; Other examples of combiners will be evident to those of skill in the art without undo experimentation.

"Comparator" in this context refers to a logic element that compares two or more inputs to produce one or more outputs that reflects similarity or difference of the inputs. An example of a hardware comparator is an operational amplifier that outputs a signal indicating whether one input is greater, less than, or about equal to the other. An example software or firmware comparator is: if (input1==input2) output=val1; else if (input1>input2) output=val2; else output=val3; Many other examples of comparators will be evident to those of skill in the art, without undo experimentation.

"Correlator" in this context refers to a logic element that identifies a configured association between its inputs. One examples of a correlator is a lookup table (LUT) configured in software or firmware. Correlators may be implemented as relational databases. An example LUT correlator is: |low_alarm_condition|low_threshold_value|0||safe_condition|safe_lower_bound|safe_upper_bound||high_alarm_condition|high_threshold_value|0| Generally, a correlator receives two or more inputs and produces an output indicative of a mutual relationship or connection between the inputs. Examples of correlators that do not use LUTs include any of a broad class of statistical correlators that identify dependence between input variables, often the extent to which two input variables have a linear relationship with each other. One commonly used statistical correlator is one that computes Pearson's product-moment coefficient for two input variables (e.g., two digital or analog input signals). Other well-known correlators compute a distance correlation, Spearman's rank correlation, a randomized dependence correlation, and Kendall's rank correlation. Many other examples of correlators will be evident to those of skill in the art, without undo experimentation.

"Firmware" in this context refers to software logic embodied as processor-executable instructions stored in read-only memories or media.

"Hardware" in this context refers to logic embodied as analog or digital circuitry.

"Incrementer" in this context refers to logic to advance (increase or decrease) a counting or index value by a fixed or predictably variable amount. Examples of hardware incrementers include adder arithmetic circuits and counter circuits. An example of a software incrementer is: x=x+incrementValue. Incrementers may be used as counters, or as logic to advance a referencial or associative index in a memory data structure.

"Logic" in this context refers to machine memory circuits, non transitory machine readable media, and/or circuitry which by way of its material and/or material-energy configuration comprises control and/or procedural signals, and/or settings and values (such as resistance, impedance, capacitance, inductance, current/voltage ratings, etc.), that may be applied to influence the operation of a device. Magnetic media, electronic circuits, electrical and optical memory (both volatile and nonvolatile), and firmware are examples of logic. Logic specifically excludes pure signals or software per se (however does not exclude machine memories comprising software and thereby forming configurations of matter).

"Parser" in this context refers to logic that divides an amalgamated input sequence or structure into multiple individual elements. Example hardware parsers are packet header parsers in network routers and switches. An example software or firmware parser is: aFields=split ("val1, val2, val3", ","); Another example of a software or firmware parser is: readFromSensor gpsCoordinate; x_pos=gpsCoordinate.x; y_pos=gpsCoordinate.y; z_pos=gpsCoordinate.z; Other examples of parsers will be readily apparent to those of skill in the art, without undo experimentation.

"Programmable device" in this context refers to an integrated circuit designed to be configured and/or reconfigured after manufacturing. The term "programmable processor" is another name for a programmable device herein. Programmable devices may include programmable processors, such as field programmable gate arrays (FPGAs), configurable hardware logic (CHL), and/or any other type programmable devices. Configuration of the programmable device is generally specified using a computer code or data such as a hardware description language (HDL), such as for example Verilog, VHDL, or the like. A programmable device may include an array of programmable logic blocks and a hierarchy of reconfigurable interconnects that allow the programmable logic blocks to be coupled to each other according to the descriptions in the HDL code. Each of the programmable logic blocks may be configured to perform complex combinational functions, or merely simple logic gates, such as AND, and XOR logic blocks. In most FPGAs, logic blocks also include memory elements, which may be simple latches, flip-flops, hereinafter also referred to as "flops," or more complex blocks of memory. Depending on the length of the interconnections between different logic blocks, signals may arrive at input terminals of the logic blocks at different times.

"Selector" in this context refers to a logic element that selects one of two or more inputs to its output as determined by one or more selection controls. Examples of hardware selectors are multiplexers and demultiplexers. An example software or firmware selector is: if (selection_control==true) output=input1; else output=input2; Many other examples of selectors will be evident to those of skill in the art, without undo experimentation.

"Sequencer" in this context refers to logic to generate an ordered list of outputs from either an unordered or partially ordered set of inputs, or from a starting input and rules to generate next inputs. One attribute of a sequencer is that the outputs are done sequentially, meaning one after the other in time. An example of a hardware sequencer is a multiplexer with a counter driving its selection input. An example of a software or firmware sequencer is: out=val++; Other examples of hardware and software or firmware sequencers will now be readily apparent to those of skill in the relevant arts.

"Software" in this context refers to logic implemented as processor-executable instructions in a machine memory (e.g. read/write volatile or nonvolatile memory or media).

"Switch" in this context refers to logic to select one or more inputs to one or more outputs under control of one or more selection signals. Examples of hardware switches are mechanical electrical switches for switching power to circuits, devices (e.g., lighting), or motors. Other examples of hardware switches are solid-state switches such as transistors. An example of a hardware or firmware switch is: if (selection==true) output=input; else output=0; A somewhat more complicated software/firmware switch is: if (selection1==true and selection2==true) output=input1; else if (selection1==true and selection2==false) output=input2; else if (selection1==false and selection2==true) output=input3; else output=noOp; Switches operate similarly to selectors in many ways (see the definition of Selector), except in some cases switches may select all inputs to the output(s) not select among inputs. Other examples of switches will be readily apparent to those having skill in the art, without undo experimentation.

Disclosed herein are embodiments of a method and system for rapid numbering of graphical elements of a drawings panel on a graphical user interface. The rapid numbering involves generating a location action in response to an action performed on a machine interface, and generating a first geometric location from the location action by applying to the location action a geometric locator. A sequencer is configured with a numbering schema to generate an element number, and a correlator is configured with the first geometric location and the element number to associate the first geometric location with the element number. The element number is added to a number set, and the element number is displayed on the drawings panel at coordinates corresponding to the first geometric location.

Generating the first geometric location from the location action may include calculating a first axis geometric location and/or calculating a second axis geometric location.

The numbering schema may delineate a starting number and a counting increment between numbers.

Configuring the correlator may further include providing a tolerance, applying the geometric locator to any unnumbered graphical element to generate a second geometric location, and configuring the correlator to associate the second geometric location with the first geometric location, if the first geometric location is within the tolerance of the second geometric location. The tolerance may be defined at least in part by the dimensions of the drawings panel.

A non-transitory computer-readable storage medium may include instructions that, when processed by a computer including a processor and a memory for storing the instructions, configure the computer to perform the method embodiments disclosed herein.

The tolerance may operate as user defined region in the drawings panel associated with an element number. The tolerance may be set by a series of action sequence inputs received through the machine interface and corresponding to a series of geometric locations defining a perimeter within the multilayered graphical document. The series of geometric locations may define a perimeter surrounding a previously placed element number.

The action sequence input may be accomplished as a combination of inputs received from at least one user interfacing devices (e.g., mouse clicks, keyboard inputs, etc.) that may be entered once (e.g., toggled) or held while receiving a second input from the at least one user interfacing devices to activate a location action.

In an embodiment, the action sequence input may be operated as a set of user inputs received through the machine interface with a cursor position on the drawings panel in the user interface defining a location action. The location action may then be mapped to the multilayered graphical document utilizing the geometric locator to define a geometric location on the multilayered graphical document.

The graphical illustration may be accomplished by a raster image positioned on a visual layer of a multilayered graphical document. The graphical illustrations may be treated as graphical objects and in a controlled memory structure with association to an element number. The graphical illustration may be repositioned and resized while in the multilayered graphical document displayed in the drawings panels. The graphical illustration may be positioned on a lower z-index layer to the element numbers and graphical connector in order to display element numbers and connector links an overlay to the graphical illustration. The multilayered graphical document may include at least one graphical illustration. The graphical illustrations may be position on different z-indexed layers, but may be reconfigured by user inputs. In some embodiments, some of the graphical illustrations may be configured by user inputs onto same z-indexed layer as the graphical connector and the element numbers.

The multilayered graphical document may be operated as a document object with at least a first layer for a graphical illustration and a second layer for displaying element number and connector lines. The multilayered graphical document may be configured to carry associations with another multilayered graphical document in such that element numbers and graphical illustrations may display consistency across at least two different multilayered graphical documents.

The counting increment may include a numerical increment configured by the multilayered graphical document and/or by placement of element numbers in the multilayered graphical document. The counting increment may be configured by the user inputs to increase by magnitude or by a set numerical value when placing an element number on the multilayered graphical document.

The cursor's position may be accomplished by the coordinate position of a cursor on the drawings panel through user interface. Due to differences in aspect ratio and display size, the machine values for the cursor position may vary between devices. The cursor's position on the drawings panel is mapped to the displayed area of the multilayered graphical document to generate a geometric location for location actions.

The drawings panel may be operated in the graphical user interface as a viewport for the multilayered graphical document. In some embodiments, the drawings panel may be configured to operate as the tolerance for associating a first geometric location with a second geometric location. When operating as the viewport, the drawings panel may partially display a section of the multilayered graphical document. The displayed section of the multilayered graphical document may be utilized to set as the tolerance for the associating a first geometric location with at least another geometric location.

The geometric region may include a region of the multilayered graphical document defined by a series of location action delineating a perimeter. The geometric region may operate as the tolerance for a first geometric location for establishing associations with at least another geometric location. The geometric region may be included with a graphical illustration, allowing the graphical illustration to be treated as a graphical object within a multilayered graphical document. The geometric region may be utilized to define placement of an element number within the geometric region or peripherally positioned to the geometric region.

The graphical connector may be operated as a graphical object displaying a line or curve connecting at least two geometric locations. The graphical connector may be displayed connecting a first geometric location and a second geometric location. the graphical connector may be generated in response to receiving a sequence of action inputs associated with a first geometric location and a second sequence of action inputs defining a second geometric location.

The series of action sequence inputs may include a set of location actions with different cursor positions on the drawings panel. The series of actions sequence inputs may define a tolerance generating a geometric region from at least two action sequence inputs to form a rectangular, circular, or irregular polygon. The series of action sequence inputs may be operated to rapidly generate geometric locations for displaying element numbers as part of the numbering sequence or associated with a displayed element number when the locations actions are detected within a tolerance of a displayed element number.

The rapid sequencer for a graphical user interface 100 comprises a numbering schema 108, sequencer 106, correlator 110, number set 112, geometric locator 104, graphical user interface 114, and machine interface 102.

Figure 14:
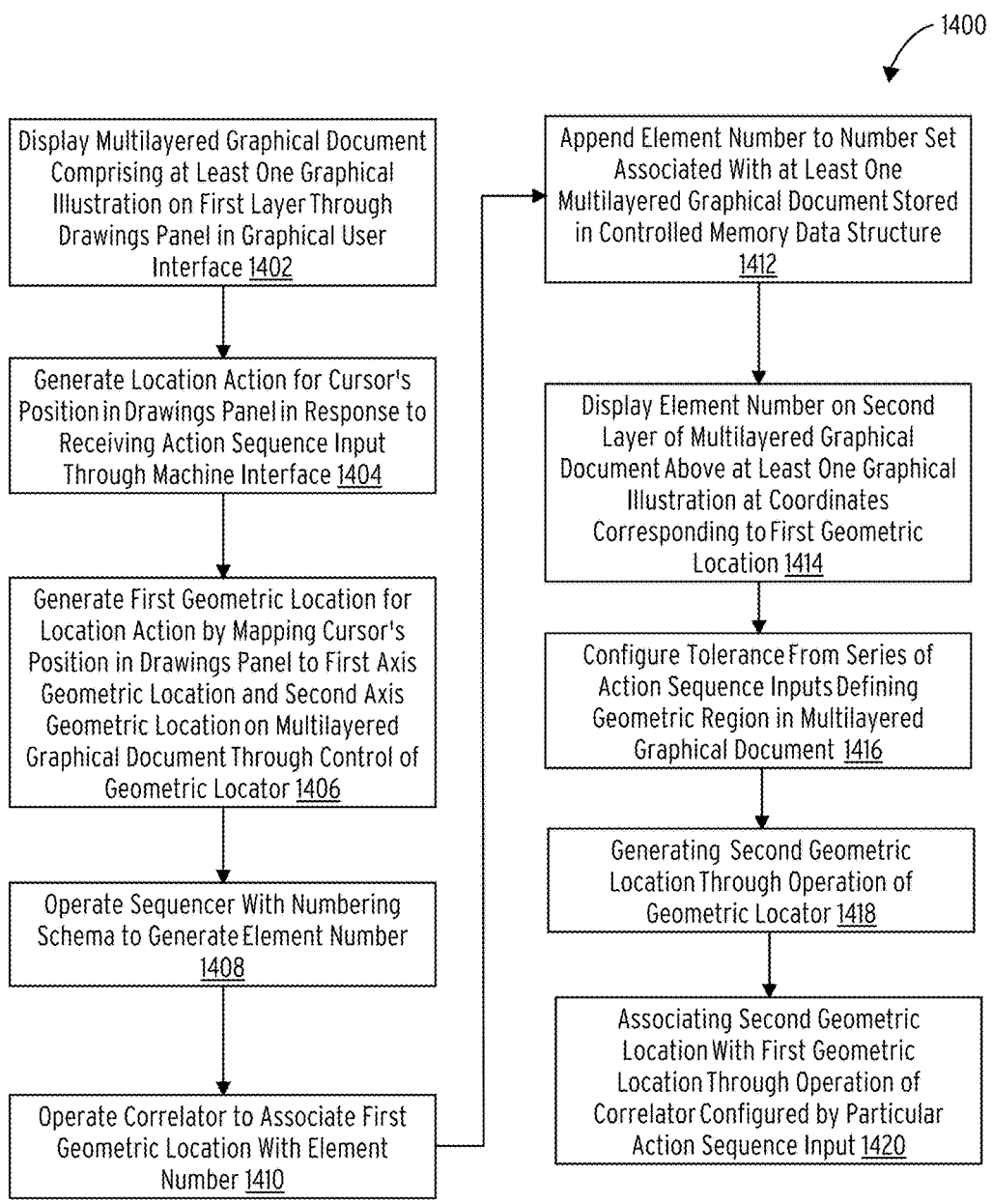
FIG. 14 illustrates an embodiment of a rapid sequencing process 1400.

The rapid sequencer for a graphical user interface 100 may be operated in accordance with the processes described in FIG. 14

Figure 2:
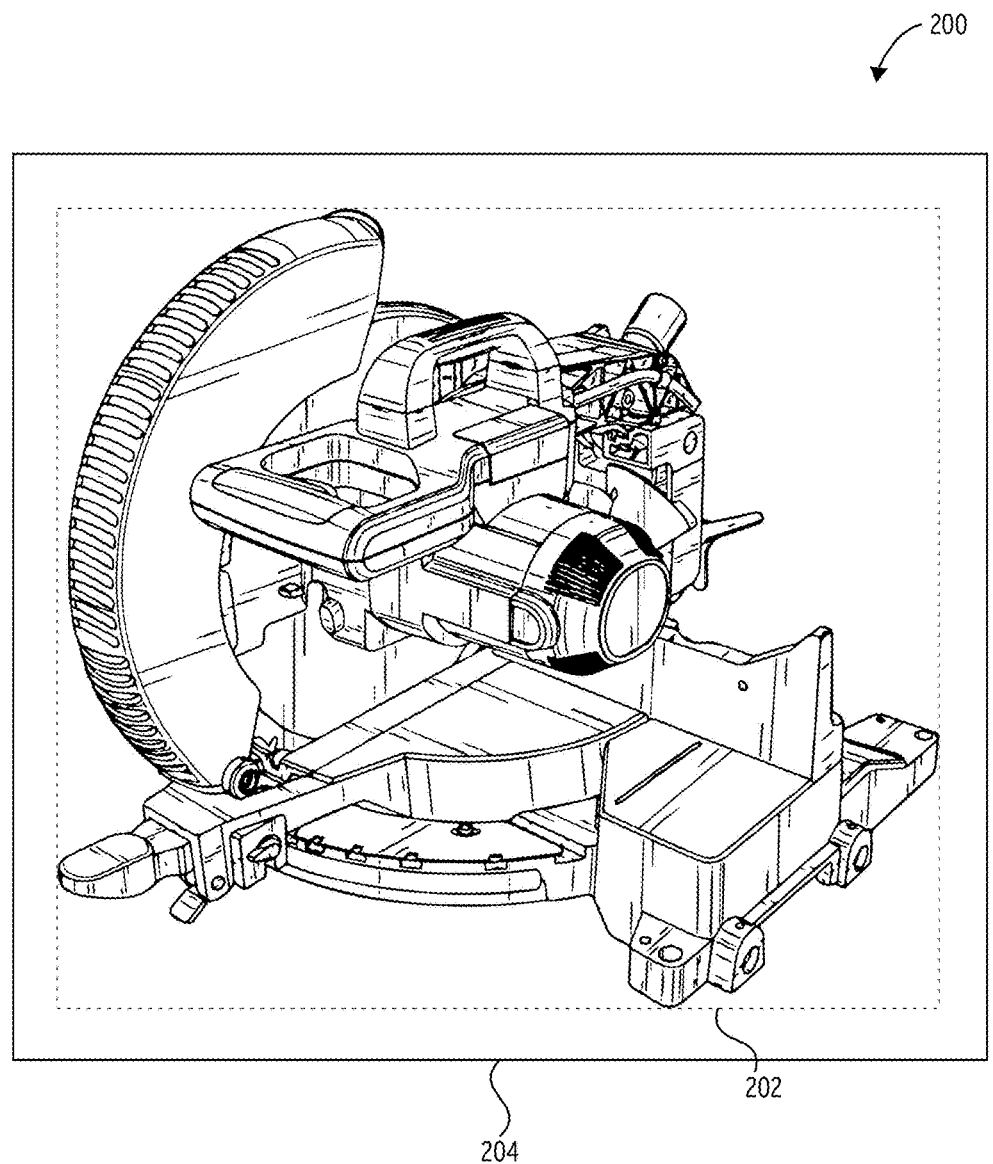
FIG. 2 illustrates a graphical illustration on a machine drawings panel 200 in accordance with one embodiment.
Figure 3:
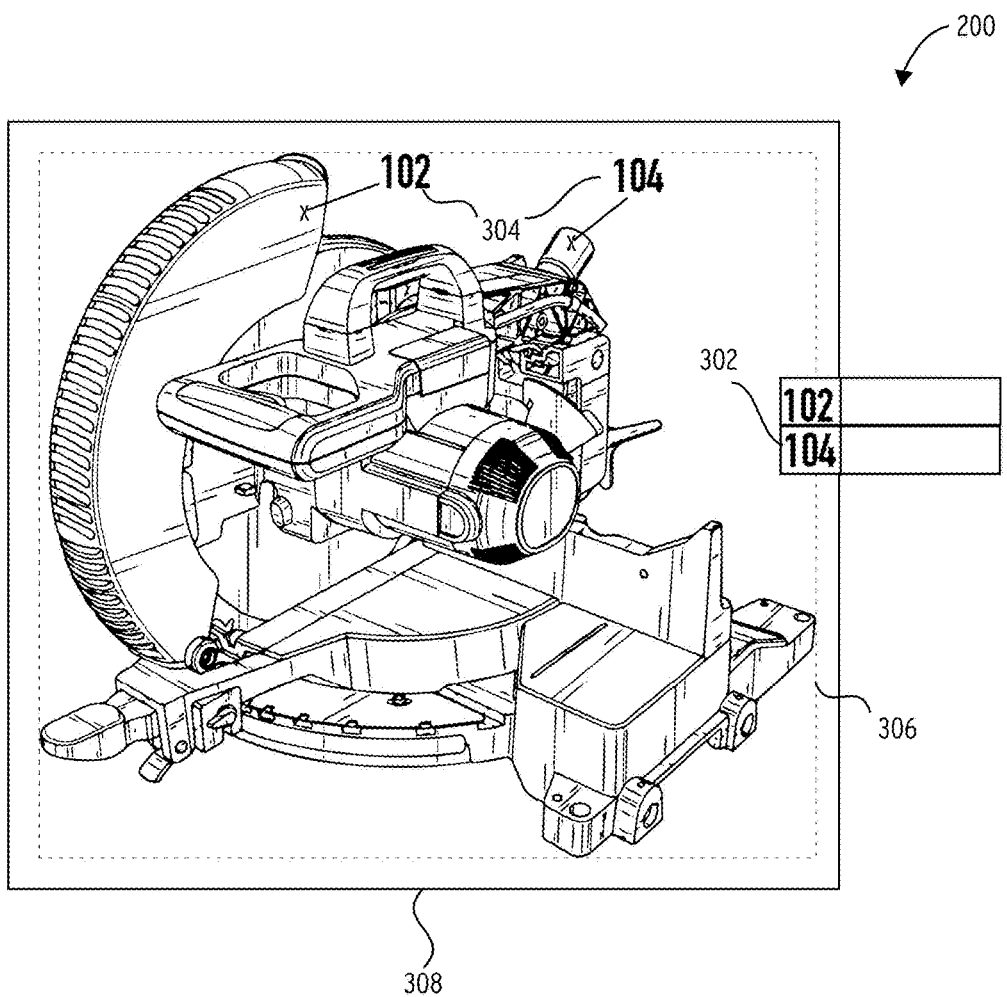
FIG. 3 illustrates operation of the rapid sequencer for a graphical user interface 100 on the graphical illustration on a machine drawings panel 200 embodiment to produce a graphical legend 302 in accordance with one embodiment.
Figure 5:
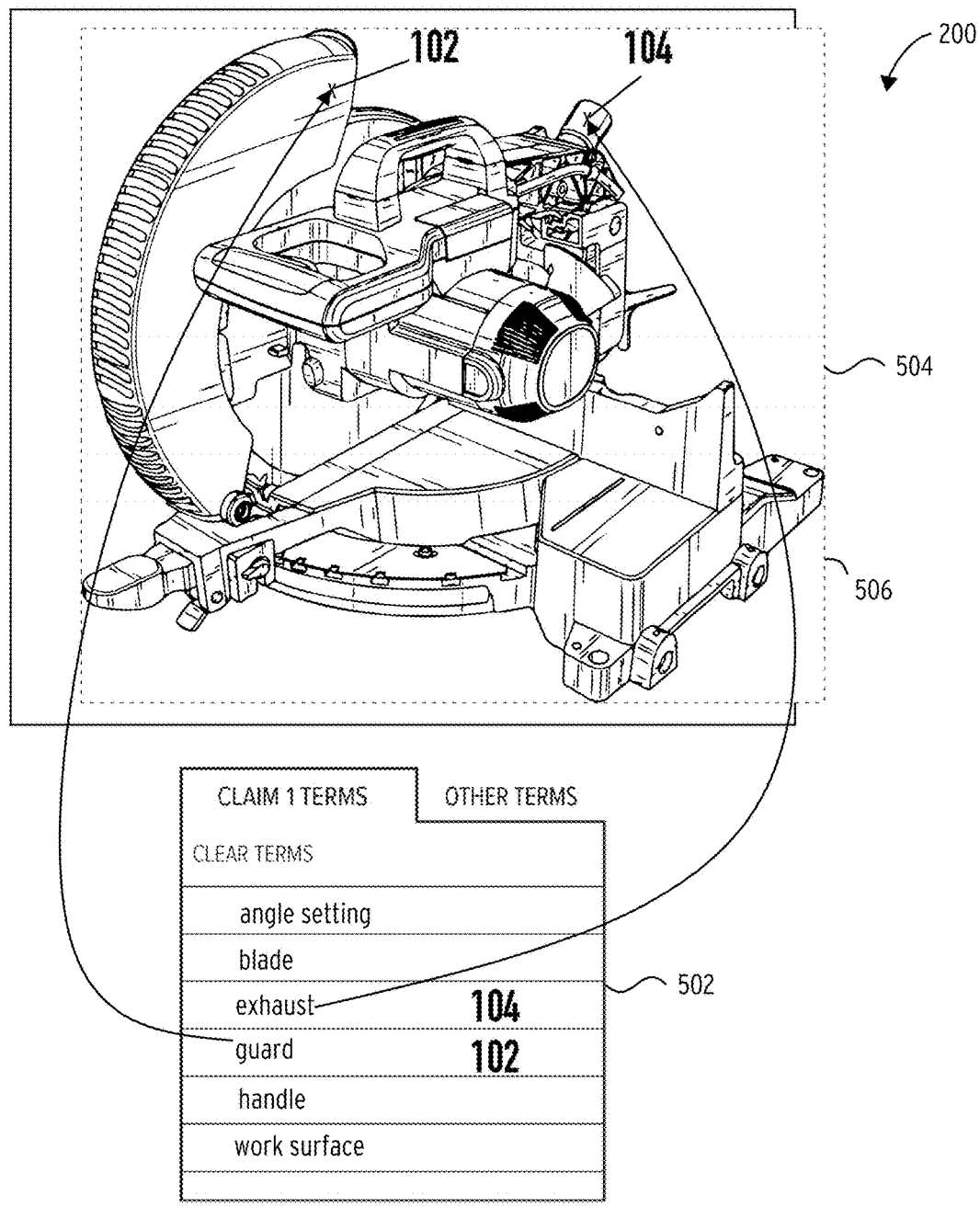
FIG. 5 illustrates operation of a rapid sequencer for a graphical user interface 100 on a graphical illustration on a machine drawings panel 200 to produce a graphical legend 502 in accordance with one embodiment.

A graphical illustration on a machine drawings panel 200 is illustrated in FIG. 2. One example of operating the rapid sequencer for a graphical user interface 100 on the graphical illustration on a machine drawings panel 200 to produce a graphical legend 302 is illustrated in FIG. 3 and FIG. 5. Another example of operating the rapid sequencer for a graphical user interface 100 to produce a graphical legend 502 is illustrated in FIG. 5.

FIG. 2 illustrates a graphical illustration on a machine drawings panel 200 in accordance with one embodiment.

FIG. 3 and FIG. 5 illustrate application of the rapid sequencer for a graphical user interface 100 for generating a graphical legend 302 on the graphical illustration on a machine drawings panel 200 in accordance with one embodiment.

A user may perform an action on a machine interface 102 and a location action is generated for each action performed on the machine interface 102. In some embodiments, the may be a click, or hovering action. In still other embodiments, the action performed may be a "drag and drop" action allowing the user to place an element such as a text box on a geometric location on. The machine interface 102 sends a location action to the geometric locator 104, which generates a first axis geometric location and a second axis geometric location. The machine interface 102 also generates an unnumbered graphical element which it transmits to correlator 110. A sequencer 106 is configured with numbering schema 108 and in response, generates an element number and transmits the element number to the correlator 110. The correlator 110 is configured by the element number transmitted from the sequencer 106 and the first axis geometric location and second axis geometric location transmitted by the geometric locator 104 to generate an element number which is added to number set 112. The graphical user interface 114 is configured with number set 112 to generate graphical legend 302 and populate graphical legend 302 with number set 112's constituent element numbers. The graphical user interface 114 then displays the the graphical legend 302 and element numbers 304. The graphical user interface 114 may receive text inputs naming elements within graphical legend 302 to further populate graphical legend 302. In some embodiments, these interactions may be repeated in rapid succession, allowing the user to automatically generate an element number for each action.

Figure 4:
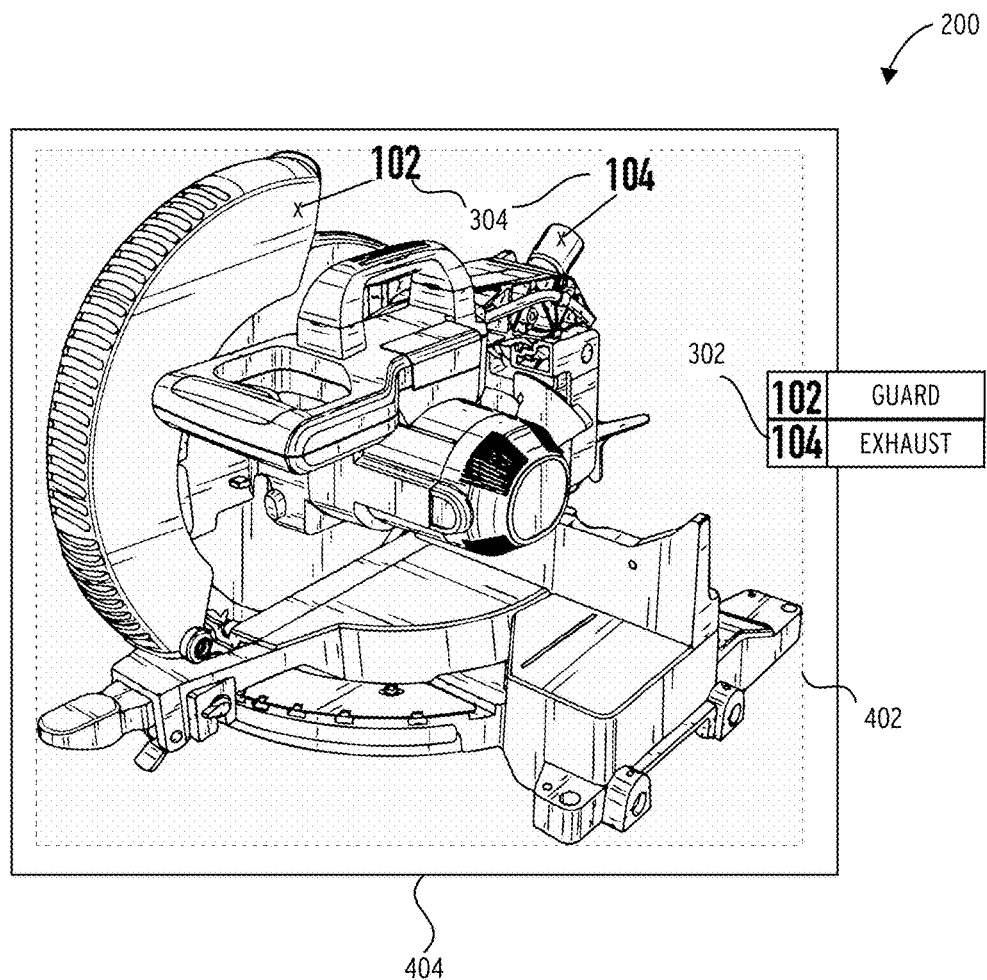
FIG. 4 illustrates operation of the rapid sequencer for a graphical user interface 100 on the graphical illustration on a machine drawings panel 200 to produce the graphical legend 302 in accordance with one embodiment.

Referencing FIG. 4, the system comprises a graphical illustration on a machine drawings panel 200, a graphical legend 302, an element numbers 304, a multilayered graphical document 402, and a drawings panel 404.

Referencing FIG. 5, the graphical illustration on a machine drawings panel 200 comprises a graphical legend 502.

In some embodiments, graphical user interface 114 within machine interface 102 may include a graphical legend 502.

The graphical legend 502 may include a list of elements, such as text labels. In some embodiments a user may interact with the elements by dragging them onto different components of a drawing. In response to this action, the rapid sequencer for a graphical user interface 100 may perform a rapid sequencing process 1300 and may then populate element numbers 304 within the graphical legend 502 to correspond to the geometric location(s) where the element(s) are dragged. These interactions may be repeated in rapid succession, allowing the user to not only automatically generate an element number for each feature of the drawing to be numbered, but also automatically associate the numbers with descriptive labels.

Figure 6:
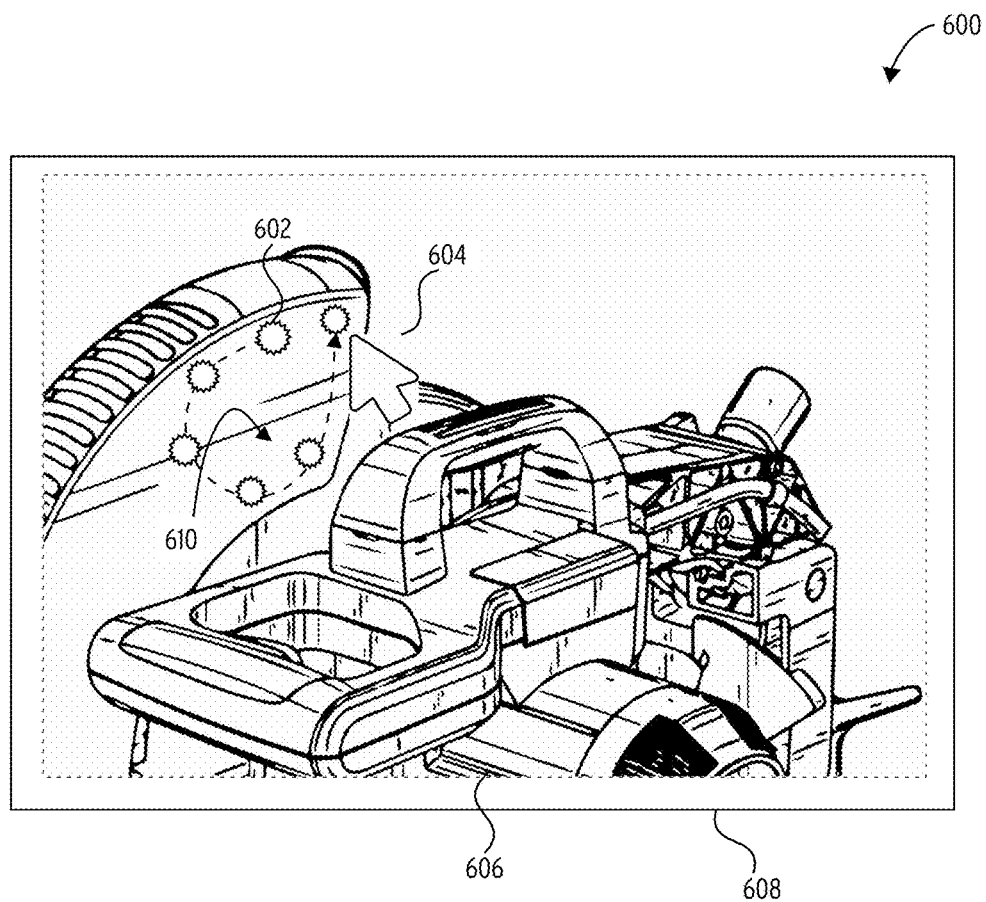
FIG. 6 illustrates an embodiment of a rapid sequencer for a graphical user interface 600.

Referencing FIG. 6, the rapid sequencer for a graphical user interface 600 comprises a series of action sequence inputs 602, a cursor 604, a multilayered graphical document 606, a drawings panel 608, and a formed geometric region 610.

The user interface may receive a series of action sequence inputs from a machine interface with a series of location action corresponding to cursor's positions on the drawings panel. The cursor's positions may be mapped to geometric locations on the multilayered graphical document. The series of action inputs define a tolerance and form a geometric region. The formed geometric region 610 may be utilized by the geometric locator and the correlator to assign an element number upon the detection of another action sequence input or cessation of previous action sequence input.

In some embodiments, the series of actions sequence inputs may generate an unnumbered geometric region. The geometric locator may be operated to detect the unnumbered geometric region and generate a geometric location to assign an element number according to the numbering schema and the number set.

Figure 8:
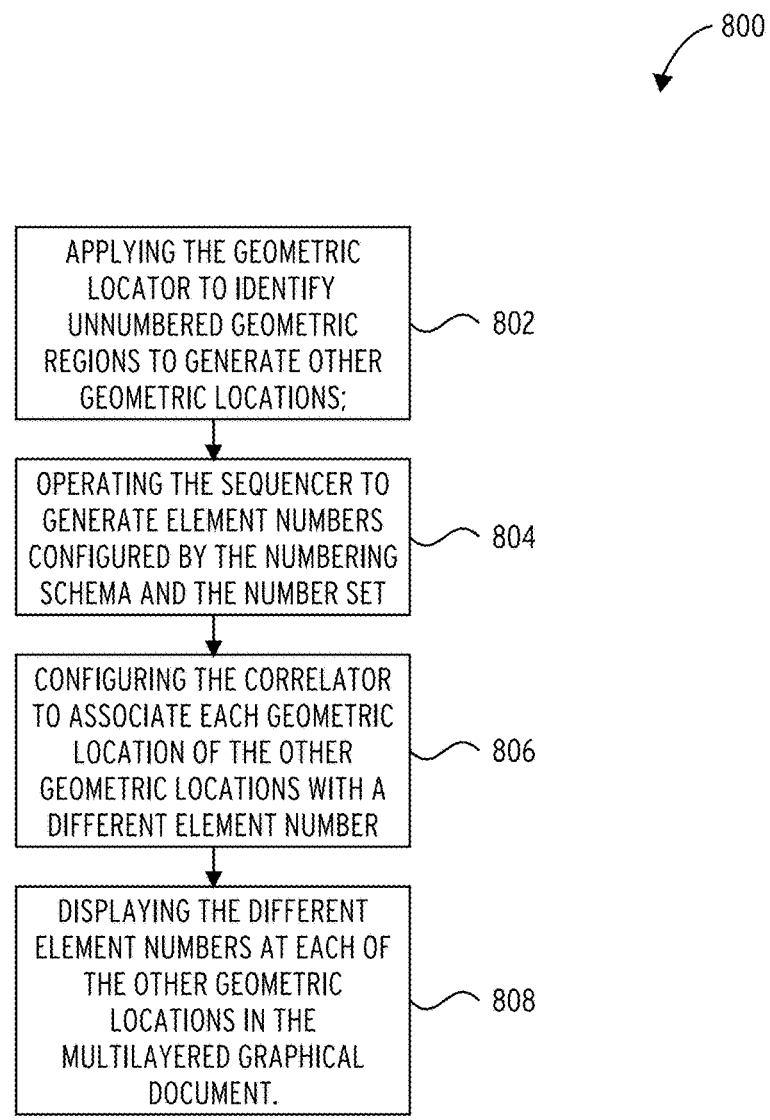
FIG. 8 illustrates an embodiment of a rapid sequencing process 800.

The rapid sequencer for a graphical user interface 600 may be operated in accordance with the process described in FIG. 8.

Figure 7:
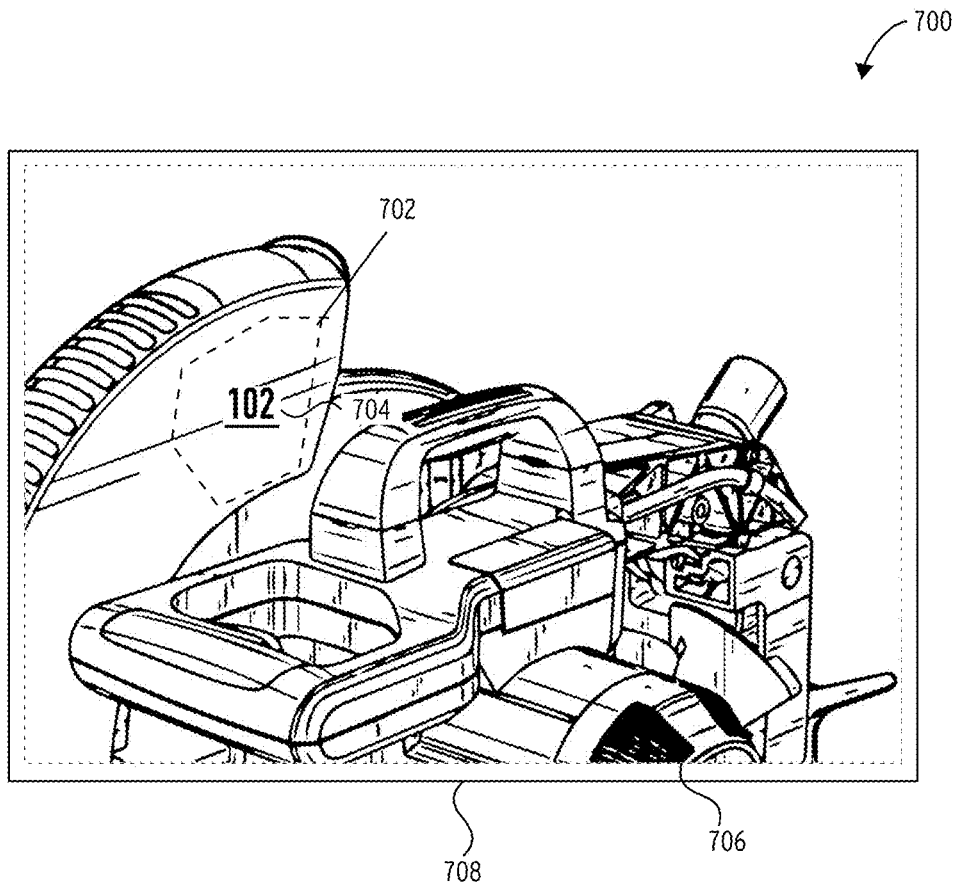
FIG. 7 illustrates an embodiment of rapid sequencer for a graphical user interface 700.

Referencing FIG. 7, The rapid sequencer for a graphical user interface 700 comprises a tolerance 702, an element number 704, a multilayered graphical document 706, and a drawings panel 708.

The rapid sequencer for a graphical user interface 700 may operated in accordance with the process described in FIG. 8.

Referencing FIG. 8, In block 802, the rapid sequencing process 800 applies the geometric locator to identify unnumbered geometric regions to generate other geometric locations. In block 804, the rapid sequencing process 800 operates the sequencer to generate element numbers configured by the numbering schema and the number set. In block 806, the rapid sequencing process 800 configures the correlator to associate each geometric location of the other geometric locations with a different element number. In block 808, the rapid sequencing process 800 displays the different element numbers at each of the other geometric locations in the multilayered graphical document.

Figure 9:
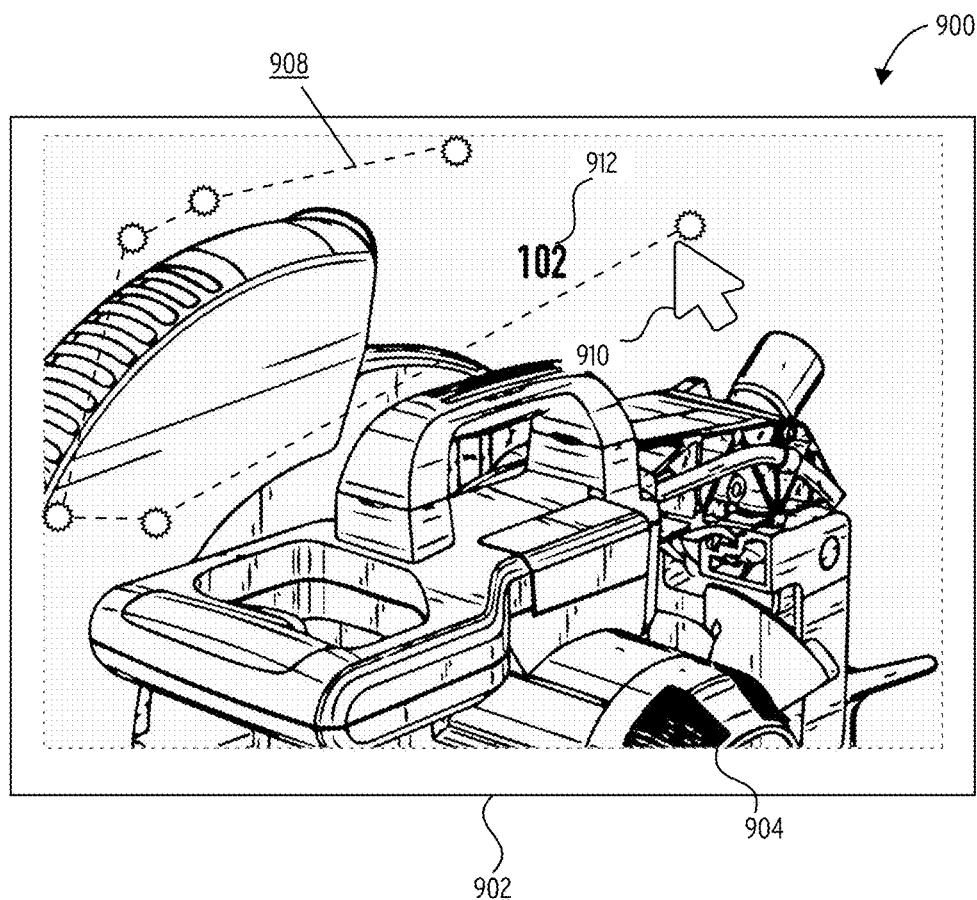
FIG. 9 illustrates an embodiment of a rapid sequencer for a graphical user interface 900.

Referencing FIG. 9, the rapid sequencer for a graphical user interface 900 comprises a drawings panel 902, a multilayered graphical document 904, a tolerance 908, a cursor 910, and an element number 912 being surrounded by a geometric region.

Figure 11:
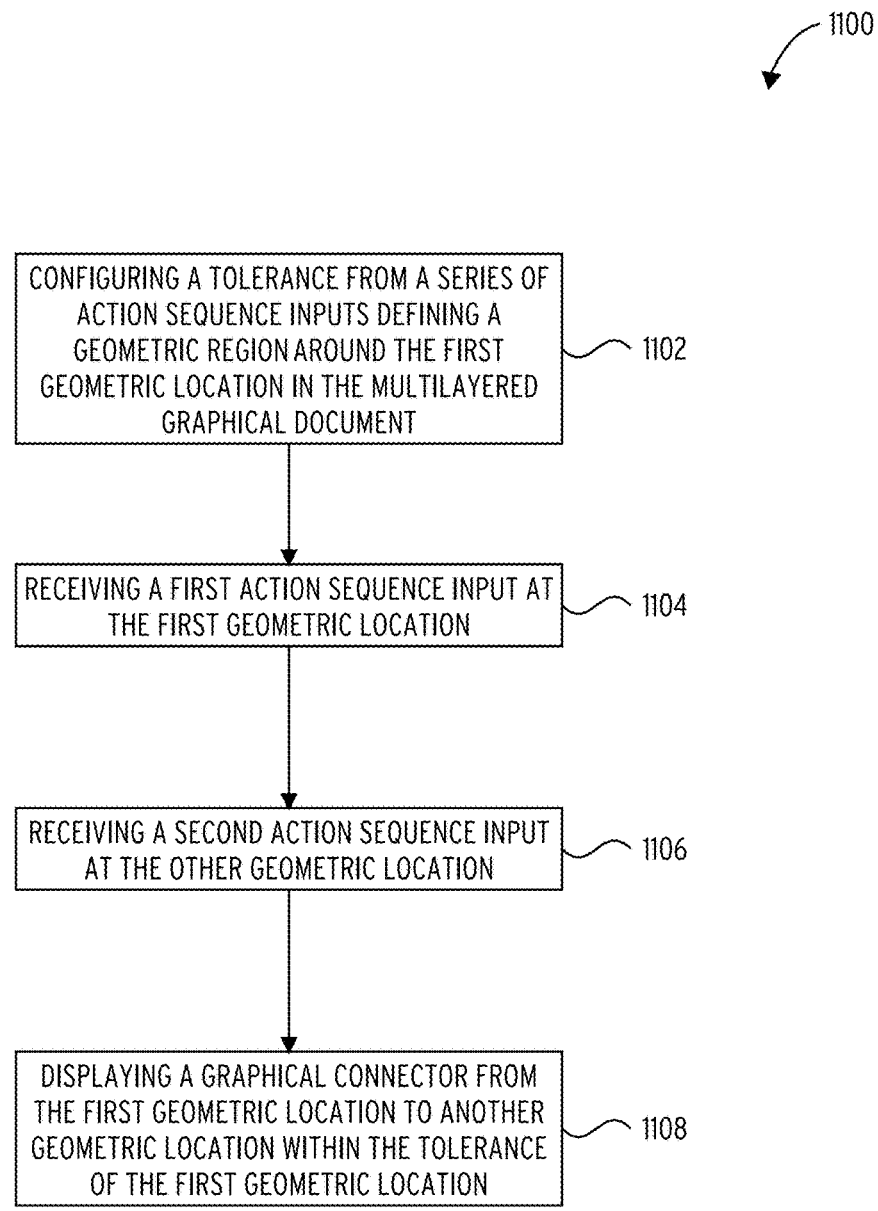
FIG. 11 illustrates an embodiment of a rapid sequencing process 1100.

The rapid sequencer for a graphical user interface 900 may be operated in accordance with the process described in FIG. 11 and FIG. 14.

Figure 10:
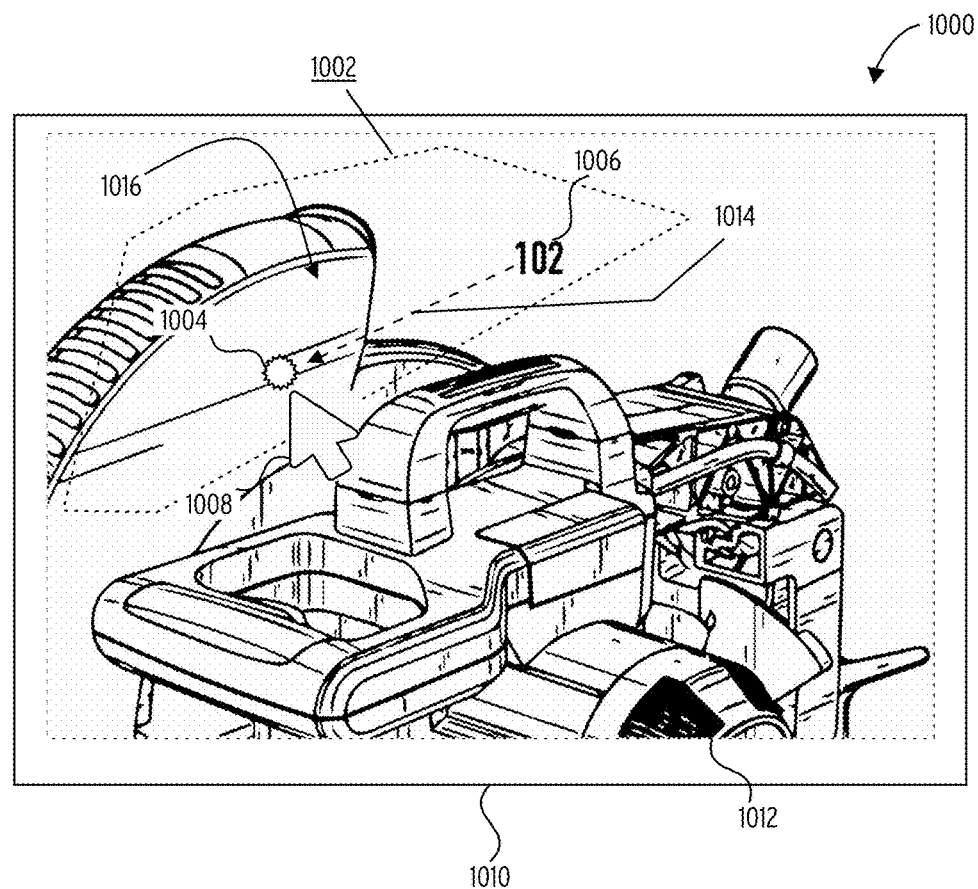
FIG. 10 illustrates an embodiment of a rapid sequencer for a graphical user interface 1000.

Referencing FIG. 10, the rapid sequencer for a graphical user interface 1000 comprises a tolerance 1002, another geometric location 1004, an element number 1006, a cursor 1008, a drawings panel 1010, a multilayered graphical document 1012, and a graphical connector 1014. The element number 1006 is positioned at the first geometric location.

The rapid sequencer for a graphical user interface 1000 may be operated in accordance with the process described in FIG. 11.

Figure 12:
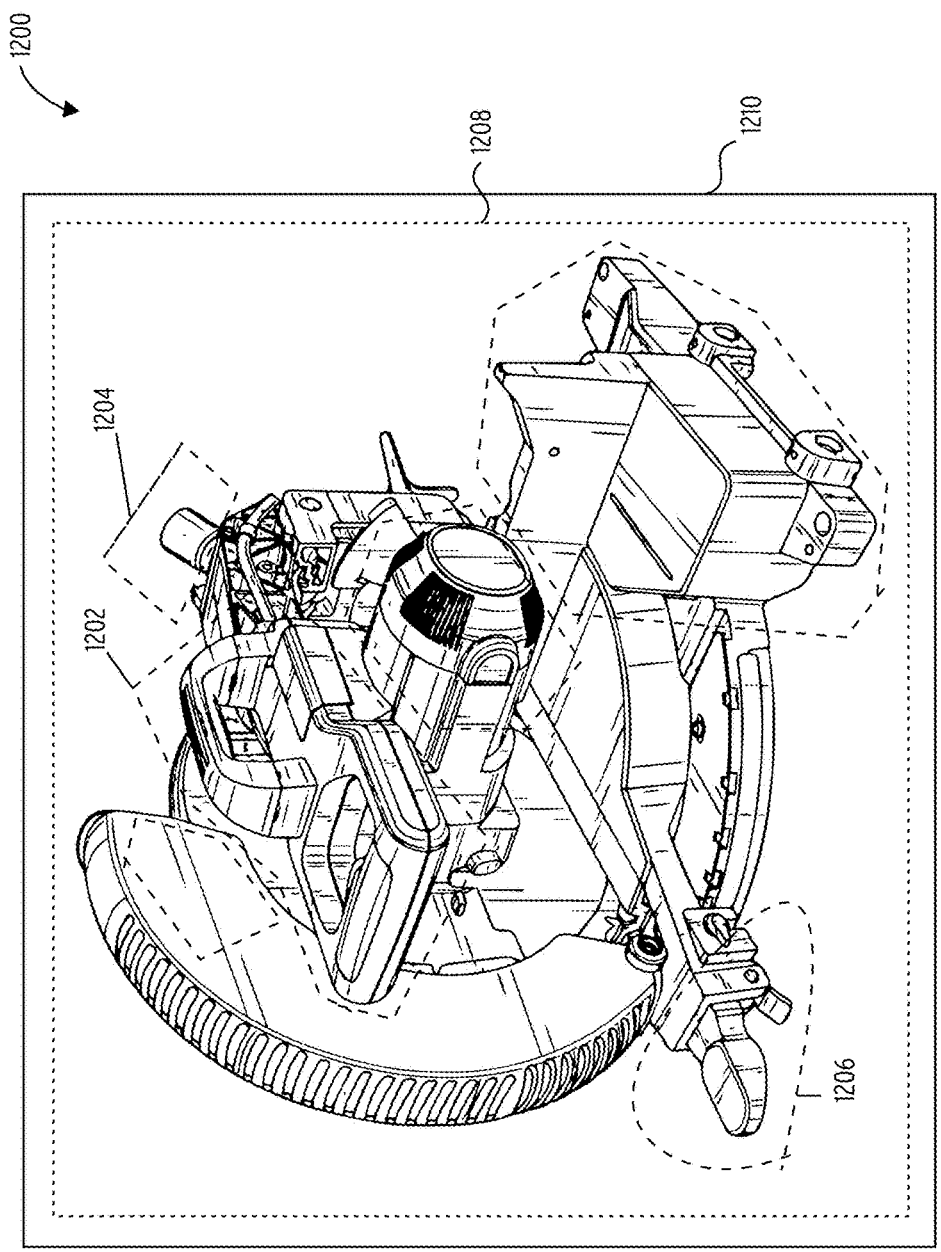
FIG. 12 illustrates an embodiment of a rapid sequencer for a graphical user interface 1200.

Referencing FIG. 11, the rapid sequencing process 1100 configures a tolerance from a series of action sequence inputs defining a geometric region around the first geometric location in the multilayered graphical document (block 1102). In block 1104, the rapid sequencing process 1100 receives a first action sequence input at the first geometric location. In block 1106, the rapid sequencing process 1100 receives a second action sequence input at the other geometric location. In block 1108, displays a graphical connector from the first geometric location to another geometric location within the tolerance of the first geometric location Referencing FIG. 12, the rapid sequencer for a graphical user interface 1200 comprises an irregular polygon tolerance region 1202, a rectangular tolerance 1204, a circular tolerance region 1206, a multilayered graphical document 1208, and a drawings panel 1210.

Figure 13:
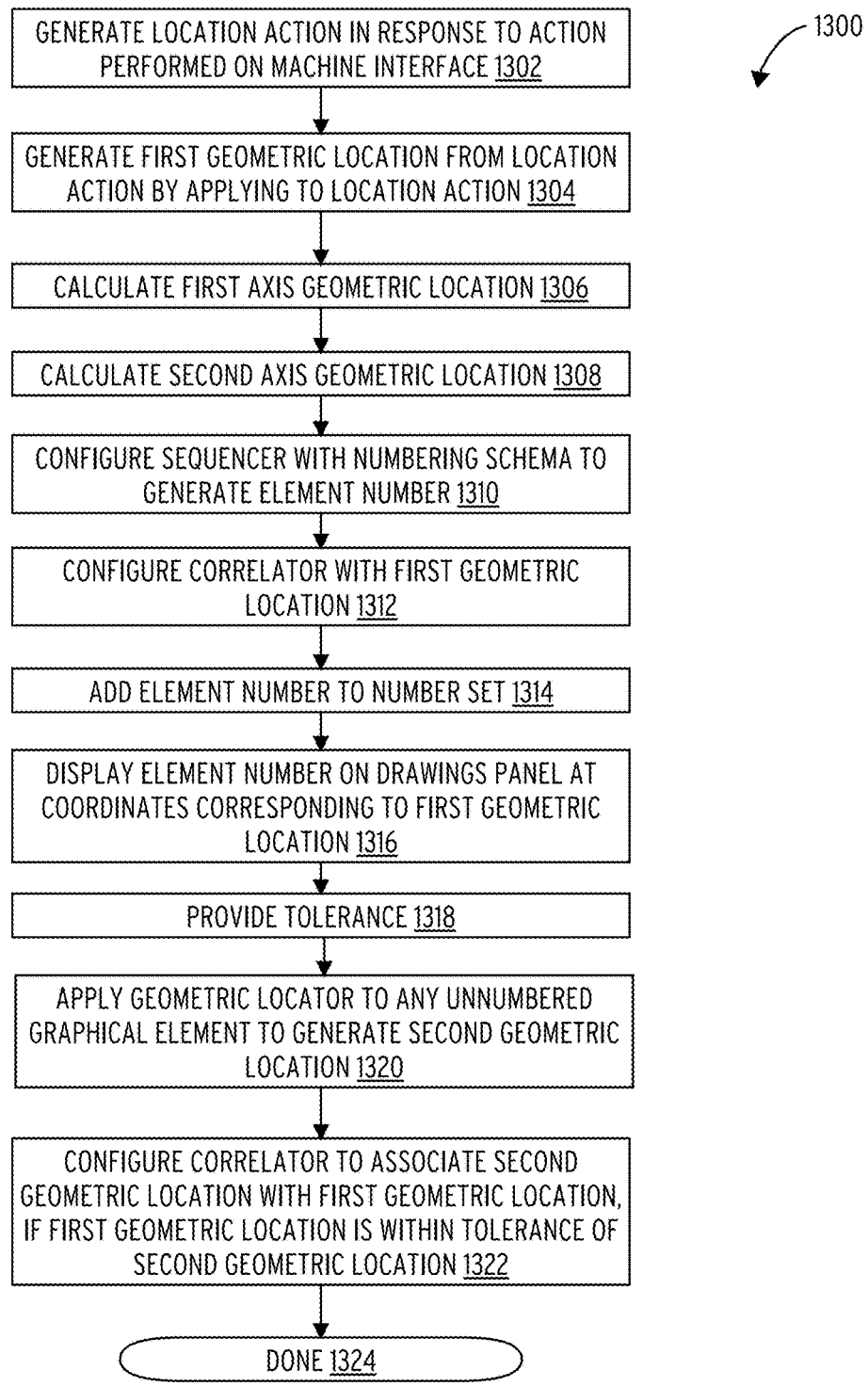
FIG. 13 illustrates a rapid sequencing process 1300 for a graphical user interface in accordance with one embodiment.

FIG. 13 illustrates a rapid sequencing process 1300 for a graphical user interface in accordance with one embodiment.

In block 1302, the rapid sequencing process 1300 generates a location action in response to an action performed on a machine interface. This may be carried out, for example, by the machine interface 102. In block 1304, the rapid sequencing process 1300 generates a first geometric location from the location action, which may be carried out, for example by applying the location action to the geometric locator 104.

In block 1306, the rapid sequencing process 1300 calculates a first axis geometric location, for example by operation of the geometric locator 104. In block 1308, the rapid sequencing process 1300 calculates a second axis geometric location, for example again by operation of the geometric locator 104.

In block 1310, the rapid sequencing process 1300 configures a sequencer with a numbering schema to generate an element number by sequencer 106. In block 1312, the rapid sequencing process 1300 configures a correlator with the first geometric location. The configuration may be carried out, for example, by the sequencer 106.

In block 1314, the rapid sequencing process 1300 adds the element number to a number set. This addition of the number may be carried out, for example, by the correlator 110.

In block 1316, the rapid sequencing process 1300 displays the element number on the drawings panel at coordinates corresponding to the first geometric location. This display may be carried out, for example, by graphical user interface 114.

In block 1318, the rapid sequencing process 1300 provides a tolerance, which may come from the correlator 110.

In block 1320, the rapid sequencing process 1300 applies the geometric locator to any unnumbered graphical element to generate a second geometric location. This application of the geometric locator may be carried out, for example, by the geometric locator 104.

In block 1322, the rapid sequencing process 1300 configures the correlator to associate the second geometric location with the first geometric location, if the first geometric location is within the tolerance of the second geometric location. The correlator 110 itself may perform this configuration.

In done block 1324, the rapid sequencing process 1300 ends.

Referencing FIG. 14, the rapid sequencing process 1400 displays a multilayered graphical document comprising at least one graphical illustration on a first layer through a drawings panel in a graphical user interface (block 1402). In block 1404, the rapid sequencing process 1400 generates a location action for a cursor's position in the drawings panel in response to receiving an action sequence input through a machine interface. In block 1406, the rapid sequencing process 1400 generates a first geometric location for the location action by mapping the cursor's position in the drawings panel to a first axis geometric location and a second axis geometric location on the multilayered graphical document through control of a geometric locator. In block 1408, the rapid sequencing process 1400 operates a sequencer with a numbering schema to generate an element number. In block 1410, the rapid sequencing process 1400 operates a correlator to associate the first geometric location with the element number. In block 1412, the rapid sequencing process 1400 appends the element number to a number set associated with at least one multilayered graphical document stored in a controlled memory data structure. In block 1414, the rapid sequencing process 1400 displays the element number on a second layer of the multilayered graphical document above the at least one graphical illustration at coordinates corresponding to the first geometric location. In block 1416, the rapid sequencing process 1400 configures a tolerance from a series of action sequence inputs defining a geometric region in the multilayered graphical document. In block 1418, the rapid sequencing process 1400 generates a second geometric location through operation of the geometric locator. In block 1420, the rapid sequencing process 1400 associates the second geometric location with the first geometric location through operation of the correlator configured by a particular action sequence input.

Figure 15:
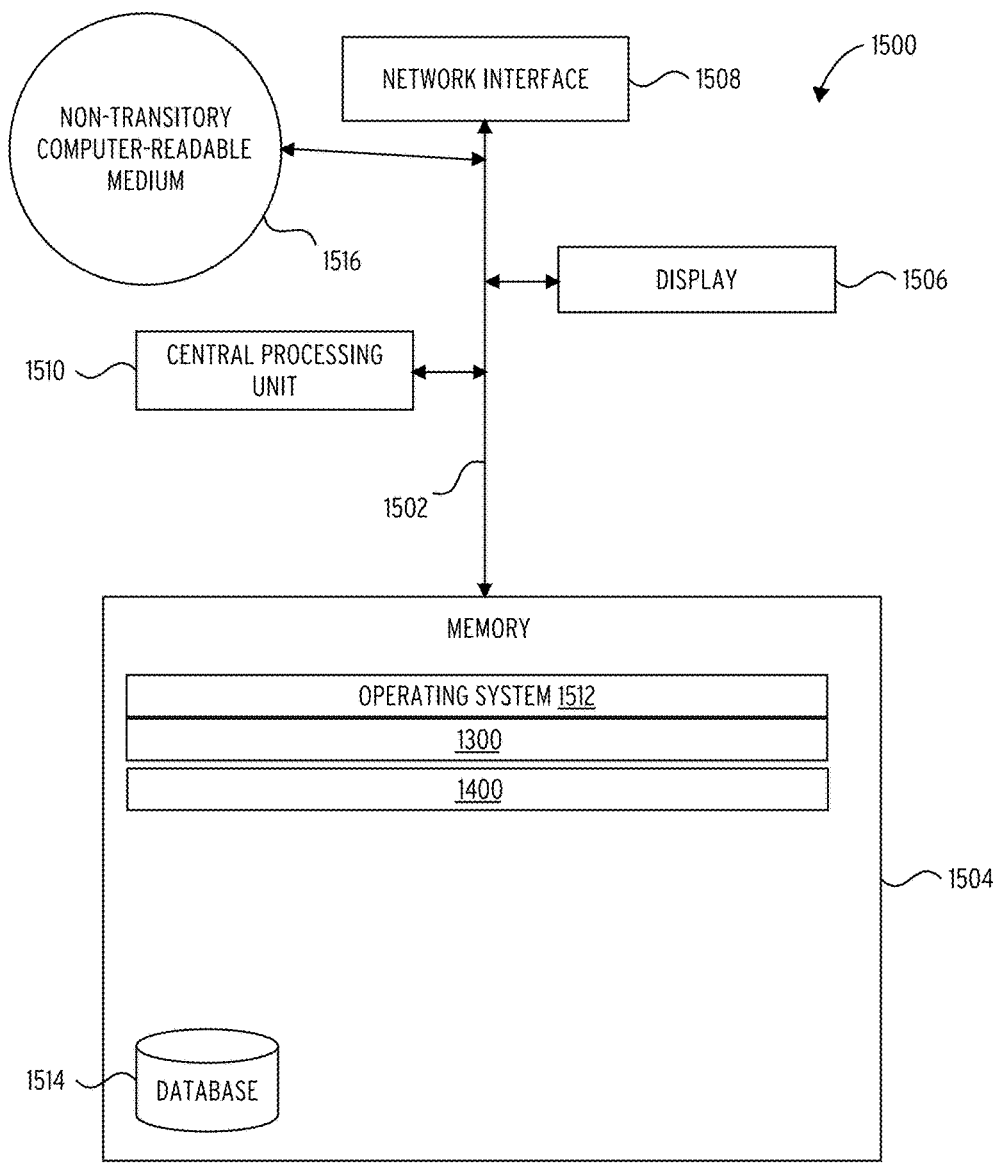
FIG. 15 illustrates a system 1500 in accordance with one embodiment.

FIG. 15 illustrates several components of an exemplary system 1500 in accordance with one embodiment. In various embodiments, the system 1500 may include a desktop PC, server, workstation, mobile phone, laptop, tablet, set-top box, appliance, or other computing device that is capable of performing operations such as those described herein. In some embodiments, the system 1500 may include many more components than those shown in FIG. 15. However, it is not necessary that all of these generally conventional components be shown in order to disclose an illustrative embodiment. Collectively, the various tangible components or a subset of the tangible components may be referred to herein as "logic" configured or adapted in a particular way, for example as logic configured or adapted with particular software or firmware.

In various embodiments, the system 1500 may comprise one or more physical and/or logical devices that collectively provide the functionalities described herein. In some embodiments, system 1500 may comprise one or more replicated and/or distributed physical or logical devices.

In some embodiments, the system 1500 may comprise one or more computing resources provisioned from a "cloud computing" provider, for example, Amazon Elastic Compute Cloud ("Amazon EC2"), provided by Amazon.com, Inc. of Seattle, Wash.; Sun Cloud Compute Utility, provided by Sun Microsystems, Inc. of Santa Clara, Calif.; Windows Azure, provided by Microsoft Corporation of Redmond, Wash., and the like.

System 1500 includes a bus 1502 interconnecting several components including a network interface 1508, a display 1506, a central processing unit 1510, and a memory 1504.

Memory 1504 generally comprises a random access memory ("RAM") and permanent non-transitory mass storage device, such as a hard disk drive or solid-state drive. Memory 1504 stores an operating system 1512, a rapid sequencing process 1300, and a rapid sequencing process 1400.

These and other software components may be loaded into memory 1504 of system 1500 using a drive mechanism (not shown) associated with a non-transitory computer-readable medium 1516, such as a floppy disc, tape, DVD/CD-ROM drive, memory card, or the like.

Memory 1504 also includes database 1514. In some embodiments, system 1500 may communicate with database 1514 via network interface 1508, a storage area network ("SAN"), a high-speed serial bus, and/or via the other suitable communication technology.

In some embodiments, the database 1514 may comprise one or more storage resources provisioned from a "cloud storage" provider, for example, Amazon Simple Storage Service ("Amazon S3"), provided by Amazon.com, Inc. of Seattle, Wash., Google Cloud Storage, provided by Google, Inc. of Mountain View, Calif., and the like.

Figure 16:
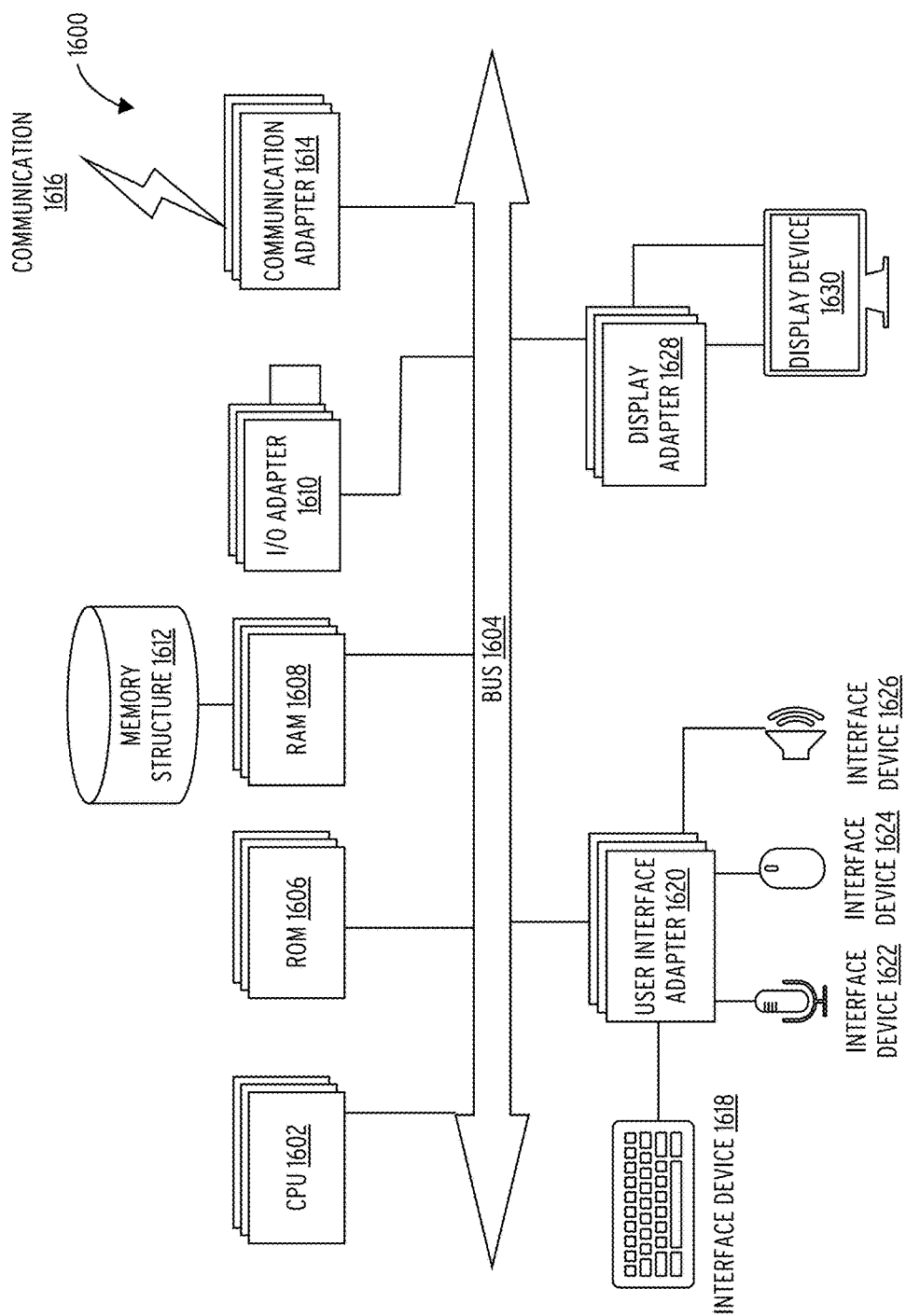
FIG. 16 illustrates an embodiment of a computing environment 1600.

Referring to FIG. 16, a computing environment 1600 comprises a CPU 1602, a bus 1604, a ROM 1606, a RAM 1608, an I/O adapter 1610, a memory structure 1612, a communication adapter 1614, a communication 1616, an interface device 1618, a user interface adapter 1620, an interface device 1622, an interface device 1624, an interface device 1626, a display adapter 1628, and a display device 1630.

Those having skill in the art will appreciate that there are various logic implementations by which processes and/or systems described herein can be effected (e.g., hardware, software, or firmware), and that the preferred vehicle will vary with the context in which the processes are deployed. If an implementer determines that speed and accuracy are paramount, the implementer may opt for a hardware or firmware implementation; alternatively, if flexibility is paramount, the implementer may opt for a solely software implementation; or, yet again alternatively, the implementer may opt for some combination of hardware, software, or firmware. Hence, there are numerous possible implementations by which the processes described herein may be effected, none of which is inherently superior to the other in that any vehicle to be utilized is a choice dependent upon the context in which the implementation will be deployed and the specific concerns (e.g., speed, flexibility, or predictability) of the implementer, any of which may vary. Those skilled in the art will recognize that optical aspects of implementations may involve optically-oriented hardware, software, and or firmware.

Those skilled in the art will appreciate that logic may be distributed throughout one or more devices, and/or may be comprised of combinations memory, media, processing circuits and controllers, other circuits, and so on. Therefore, in the interest of clarity and correctness logic may not always be distinctly illustrated in drawings of devices and systems, although it is inherently present therein. The techniques and procedures described herein may be implemented via logic distributed in one or more computing devices. The particular distribution and choice of logic will vary according to implementation.

The foregoing detailed description has set forth various embodiments of the devices or processes via the use of block diagrams, flowcharts, or examples. Insofar as such block diagrams, flowcharts, or examples contain one or more functions or operations, it will be understood as notorious by those within the art that each function or operation within such block diagrams, flowcharts, or examples can be implemented, individually or collectively, by a wide range of hardware, software, firmware, or virtually any combination thereof. Portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in standard integrated circuits, as one or more computer programs running on one or more processing devices (e.g., as one or more programs running on one or more computer systems), as one or more programs running on one or more processors (e.g., as one or more programs running on one or more microprocessors), as firmware, or as virtually any combination thereof, and that designing the circuitry or writing the code for the software or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies equally regardless of the particular type of signal bearing media used to actually carry out the distribution. Examples of a signal bearing media include, but are not limited to, the following: recordable type media such as floppy disks, hard disk drives, CD ROMs, digital tape, flash drives, SD cards, solid state fixed or removable storage, and computer memory.

In a general sense, those skilled in the art will recognize that the various aspects described herein which can be implemented, individually or collectively, by a wide range of hardware, software, firmware, or any combination thereof can be viewed as being composed of various types of circuitry.

Those skilled in the art will recognize that it is common within the art to describe devices or processes in the fashion set forth herein, and thereafter use standard engineering practices to integrate such described devices or processes into larger systems. At least a portion of the devices or processes described herein can be integrated into a network processing system via a reasonable amount of experimentation. Various embodiments are described herein and presented by way of example and not limitation.

What is claimed is:

1. A method for rapid numbering of a multilayered graphical document on a graphical user interface comprising:
displaying the multilayered graphical document comprising at least one graphical illustration on a first layer through a drawings panel in a graphical user interface;
generating a location action for a cursor's position in the drawings panel in response to receiving an action sequence input through a machine interface;
generating a first geometric location on the graphical user interface for the location action by mapping the cursor's position in the drawings panel to a first axis geometric location and a second axis geometric location on the multilayered graphical document through control of a geometric locator;
operating a sequencer with a numbering schema to generate an element number;

operating a correlator to associate the first geometric location with the element number;

appending the element number to a number set associated with at least one multilayered graphical document stored in a controlled memory data structure;

displaying the element number on a second layer of the multilayered graphical document above the at least one graphical illustration at coordinates corresponding to the first geometric location;

configuring a tolerance from a series of action sequence inputs defining a geometric region in the multilayered graphical document;

generating a second geometric location on the graphical user interface through operation of the geometric locator; and associating the second geometric location with the first geometric location through operation of the correlator configured by a particular action sequence input.

2. The method for rapid numbering of claim 1 further comprising:

configuring the tolerance at least in part by the dimensions of the drawings panel;

applying the geometric locator to any unnumbered graphical element to generate a second geometric location;

configuring the correlator to associate the second geometric location with the first geometric location, if the first geometric location is within the tolerance of the second geometric location; and displaying a graphical connector linking the element number of the first geometric location with the second geometric location.

3. The method for rapid numbering of claim 1 further comprising:

displaying a graphical connector from the first geometric location to another geometric location within the tolerance of the first geometric location in response to receiving a first action sequence input at the first geometric location and a second action sequence input at the other geometric location.

4. The method for rapid numbering of claim 1 further comprising:

applying the geometric locator to identify unnumbered geometric regions to generate other geometric locations;

operating the sequencer to generate element numbers configured by the numbering schema and the number set;

configuring the correlator to associate each geometric location of the other geometric locations with a different element number; and displaying different element numbers at each of the other geometric locations in the multilayered graphical document.

5. The method for rapid numbering of claim 1 further comprising:

the numbering schema delineating a starting number and a counting increment between numbers.

* * * * *